United States Patent
Franer et al.

(10) Patent No.: US 8,771,307 B2
(45) Date of Patent: *Jul. 8, 2014

(54) DUCKBILL SEAL WITH FLUID DRAINAGE FEATURE

(75) Inventors: Paul T. Franer, Cincinnati, OH (US); Thomas A. Gilker, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 234 days.

This patent is subject to a terminal disclaimer.

(21) Appl. No.: 13/353,075

(22) Filed: Jan. 18, 2012

(65) Prior Publication Data

US 2012/0116313 A1  May 10, 2012

Related U.S. Application Data

(63) Continuation of application No. 11/771,263, filed on Jun. 29, 2007, now Pat. No. 8,100,929.

(51) Int. Cl.
*A61B 17/34* (2006.01)
(52) U.S. Cl.
USPC ............... 606/185; 604/167.03; 137/846
(58) Field of Classification Search
USPC .................. 606/185, 191, 167, 139, 108;
604/167.03, 167.06, 167.01, 237,
604/167.02, 167.04, 246, 247, 167.05,
604/164.01, 164.02, 248–250, 256;
600/184; 137/846
See application file for complete search history.

(56) References Cited

U.S. PATENT DOCUMENTS

| | | |
|---|---|---|
| 3,900,022 A | 8/1975 | Widran |
| 3,903,877 A | 9/1975 | Terada |
| 3,924,608 A | 12/1975 | Mitsui |
| 3,980,078 A | 9/1976 | Tominaga |
| 3,981,276 A | 9/1976 | Ernest |
| 4,204,563 A | 5/1980 | Pyle |
| 4,279,246 A | 7/1981 | Chikama |
| 4,687,033 A | 8/1987 | Furrow et al. |
| 4,690,140 A | 9/1987 | Mecca |

(Continued)

FOREIGN PATENT DOCUMENTS

| | | |
|---|---|---|
| CA | 2060930 A1 | 10/1992 |
| DE | 10330518 A1 | 2/2005 |

(Continued)

OTHER PUBLICATIONS

Japanese Office Action for Application No. 2010-514948, issued Nov. 6, 2012. (2 pages).

(Continued)

*Primary Examiner* — Tuan V Nguyen
*Assistant Examiner* — Tin Nguyen
(74) *Attorney, Agent, or Firm* — Nutter McClennen & Fish LLP

(57) ABSTRACT

Seal assemblies, generally for use in trocar assemblies, are provided for selectively promoting movement of fluid away from a central portion of the seal assemblies. In one exemplary embodiment, an inner surface of a seal body of the seal assembly is configured to selectively promote such movement of fluid away from the central portion of the seal body toward a peripheral portion of the seal body. While various configurations, geometries, and dimensions are discussed, one example of such a configuration includes locating a central portion of the seal body at a more proximal position than a peripheral portion of the seal body.

16 Claims, 13 Drawing Sheets

(56) References Cited

U.S. PATENT DOCUMENTS

| | | |
|---|---|---|
| 4,722,000 A | 1/1988 | Chatenever |
| 4,836,187 A | 6/1989 | Iwakoshi et al. |
| 4,877,016 A | 10/1989 | Kantor et al. |
| 4,919,305 A | 4/1990 | Podgers |
| 4,943,280 A | 7/1990 | Lander |
| 5,084,057 A | 1/1992 | Green et al. |
| 5,104,383 A | 4/1992 | Shichman |
| 5,127,909 A | 7/1992 | Shichman |
| 5,141,498 A * | 8/1992 | Christian ................ 604/167.03 |
| 5,167,220 A | 12/1992 | Brown |
| 5,180,373 A | 1/1993 | Green et al. |
| 5,191,878 A | 3/1993 | Iida et al. |
| 5,197,955 A | 3/1993 | Stephens et al. |
| 5,201,714 A | 4/1993 | Gentelia et al. |
| 5,207,213 A | 5/1993 | Auhll et al. |
| 5,209,737 A | 5/1993 | Ritchart et al. |
| 5,226,891 A | 7/1993 | Bushatz et al. |
| 5,237,984 A | 8/1993 | Williams, III et al. |
| 5,279,542 A | 1/1994 | Wilk |
| 5,312,363 A | 5/1994 | Ryan et al. |
| 5,312,397 A | 5/1994 | Cosmescu |
| 5,313,934 A | 5/1994 | Wiita et al. |
| 5,320,610 A | 6/1994 | Yoon |
| 5,326,013 A | 7/1994 | Green et al. |
| 5,330,437 A | 7/1994 | Durman |
| 5,334,164 A | 8/1994 | Guy et al. |
| 5,337,730 A | 8/1994 | Maguire |
| 5,339,800 A | 8/1994 | Wiita et al. |
| 5,342,315 A | 8/1994 | Rowe et al. |
| 5,347,988 A | 9/1994 | Hori |
| 5,354,302 A | 10/1994 | Ko |
| 5,364,002 A | 11/1994 | Green et al. |
| 5,369,525 A | 11/1994 | Bala et al. |
| 5,382,297 A | 1/1995 | Valentine et al. |
| 5,389,081 A | 2/1995 | Castro |
| 5,391,154 A | 2/1995 | Young |
| 5,392,766 A | 2/1995 | Masterson et al. |
| 5,395,342 A | 3/1995 | Yoon |
| 5,400,767 A | 3/1995 | Murdoch |
| 5,419,309 A | 5/1995 | Biehl |
| 5,441,513 A | 8/1995 | Roth |
| 5,443,452 A | 8/1995 | Hart et al. |
| 5,448,990 A | 9/1995 | De Faria-Correa |
| 5,449,370 A | 9/1995 | Vaitekunas |
| 5,458,633 A | 10/1995 | Bailey |
| 5,460,616 A | 10/1995 | Weinstein et al. |
| 5,462,100 A | 10/1995 | Covert et al. |
| 5,464,008 A | 11/1995 | Kim |
| 5,476,475 A | 12/1995 | Gadberry |
| 5,486,154 A | 1/1996 | Kelleher |
| 5,492,304 A | 2/1996 | Smith et al. |
| 5,496,280 A | 3/1996 | Vandenbroek et al. |
| 5,496,345 A | 3/1996 | Kieturakis et al. |
| 5,496,411 A | 3/1996 | Candy |
| 5,514,084 A | 5/1996 | Fisher |
| 5,514,153 A | 5/1996 | Bonutti |
| 5,518,026 A | 5/1996 | Benjey |
| 5,518,502 A | 5/1996 | Kaplan et al. |
| 5,520,655 A | 5/1996 | Davila et al. |
| 5,533,496 A | 7/1996 | De Faria-Correa et al. |
| 5,535,759 A | 7/1996 | Wilk |
| 5,536,234 A | 7/1996 | Newman |
| 5,542,931 A | 8/1996 | Gravener et al. |
| 5,545,142 A | 8/1996 | Stephens et al. |
| 5,545,179 A | 8/1996 | Williamson, IV |
| 5,549,543 A | 8/1996 | Kim |
| 5,551,448 A | 9/1996 | Matula et al. |
| 5,554,151 A | 9/1996 | inchliffe |
| 5,568,828 A | 10/1996 | Harris |
| 5,569,183 A | 10/1996 | Kieturakis |
| 5,569,205 A | 10/1996 | Hart et al. |
| 5,575,756 A | 11/1996 | Karasawa et al. |
| 5,584,850 A | 12/1996 | Hart et al. |
| 5,590,697 A | 1/1997 | Benjey et al. |
| 5,603,702 A | 2/1997 | Smith et al. |
| 5,605,175 A | 2/1997 | Bergsma et al. |
| 5,628,732 A | 5/1997 | Antoon, Jr. et al. |
| 5,630,795 A | 5/1997 | Kuramoto et al. |
| 5,634,911 A | 6/1997 | Hermann et al. |
| 5,643,301 A | 7/1997 | Mollenauer |
| 5,647,372 A | 7/1997 | Tovey et al. |
| 5,647,840 A | 7/1997 | D'Amelio et al. |
| 5,651,757 A | 7/1997 | Meckstroth |
| 5,657,963 A | 8/1997 | Hinchliffe et al. |
| 5,658,273 A | 8/1997 | Long |
| 5,685,823 A | 11/1997 | Ito et al. |
| 5,688,222 A | 11/1997 | Hluchy et al. |
| 5,709,664 A | 1/1998 | Vandenbroek et al. |
| 5,720,756 A | 2/1998 | Green et al. |
| 5,720,759 A | 2/1998 | Green et al. |
| 5,725,477 A | 3/1998 | Yasui et al. |
| 5,725,478 A | 3/1998 | Saad |
| 5,743,884 A | 4/1998 | Hasson et al. |
| 5,752,938 A | 5/1998 | Flatland et al. |
| 5,755,252 A | 5/1998 | Bergsma et al. |
| 5,755,732 A | 5/1998 | Green et al. |
| 5,782,859 A | 7/1998 | Nicholas et al. |
| 5,788,676 A | 8/1998 | Yoon |
| 5,792,044 A | 8/1998 | Foley et al. |
| 5,792,113 A | 8/1998 | Kramer et al. |
| 5,797,434 A | 8/1998 | Benjey et al. |
| 5,807,338 A | 9/1998 | Smith et al. |
| 5,814,026 A | 9/1998 | Yoon |
| 5,817,061 A | 10/1998 | Goodwin et al. |
| 5,848,992 A | 12/1998 | Hart et al. |
| 5,860,458 A | 1/1999 | Benjey et al. |
| 5,871,440 A | 2/1999 | Okada |
| 5,882,345 A | 3/1999 | Yoon |
| 5,902,264 A | 5/1999 | Toso et al. |
| 5,903,231 A | 5/1999 | Emelko |
| 5,906,595 A | 5/1999 | Powell et al. |
| 5,954,635 A | 9/1999 | Foley et al. |
| 5,957,888 A | 9/1999 | Hinchliffe |
| 5,964,781 A | 10/1999 | Mollenauer et al. |
| 5,983,958 A | 11/1999 | Bergsma et al. |
| 6,004,326 A | 12/1999 | Castro et al. |
| 6,007,487 A | 12/1999 | Foley et al. |
| 6,017,333 A | 1/2000 | Bailey |
| 6,062,276 A | 5/2000 | Benjey et al. |
| 6,063,050 A | 5/2000 | Manna et al. |
| 6,093,176 A | 7/2000 | Dennis |
| 6,110,103 A | 8/2000 | Donofrio |
| 6,126,592 A | 10/2000 | Proch et al. |
| 6,152,871 A | 11/2000 | Foley et al. |
| 6,159,182 A | 12/2000 | Davis et al. |
| 6,162,170 A | 12/2000 | Foley et al. |
| 6,167,920 B1 | 1/2001 | Enge |
| 6,176,823 B1 | 1/2001 | Foley et al. |
| 6,176,825 B1 | 1/2001 | Chin et al. |
| 6,206,057 B1 | 3/2001 | Benjey et al. |
| 6,206,822 B1 | 3/2001 | Foley et al. |
| 6,216,661 B1 | 4/2001 | Pickens et al. |
| 6,217,509 B1 | 4/2001 | Foley et al. |
| 6,253,802 B1 | 7/2001 | Enge |
| 6,264,604 B1 | 7/2001 | Kieturakis et al. |
| 6,287,313 B1 | 9/2001 | Sasso |
| 6,354,992 B1 | 3/2002 | Kato |
| 6,371,909 B1 | 4/2002 | Hoeg et al. |
| 6,409,657 B1 | 6/2002 | Kawano |
| 6,423,266 B1 | 7/2002 | Choperena et al. |
| 6,425,535 B1 | 7/2002 | Akiba |
| 6,425,859 B1 | 7/2002 | Foley et al. |
| 6,443,190 B1 | 9/2002 | Enge |
| 6,447,446 B1 | 9/2002 | Smith et al. |
| 6,482,181 B1 | 11/2002 | Racenet et al. |
| 6,494,893 B2 | 12/2002 | Dubrul et al. |
| 6,497,687 B1 | 12/2002 | Blanco |
| 6,516,835 B2 | 2/2003 | Enge |
| 6,520,907 B1 | 2/2003 | Foley et al. |
| 6,534,002 B1 | 3/2003 | Lin et al. |
| 6,551,282 B1 | 4/2003 | Exline et al. |
| 6,562,046 B2 | 5/2003 | Sasso |
| 6,569,120 B1 | 5/2003 | Green et al. |
| 6,595,915 B2 | 7/2003 | Akiba |

(56) References Cited

U.S. PATENT DOCUMENTS

| | | |
|---|---|---|
| 6,595,946 B1 | 7/2003 | Pasqualucci |
| 6,601,617 B2 | 8/2003 | Enge |
| 6,605,098 B2 | 8/2003 | Nobis et al. |
| 6,638,214 B2 | 10/2003 | Akiba |
| 6,648,906 B2 | 11/2003 | Lasheras et al. |
| 6,679,833 B2 | 1/2004 | Smith et al. |
| 6,679,834 B2 | 1/2004 | Stahl et al. |
| 6,679,837 B2 | 1/2004 | Daikuzono |
| 6,699,185 B2 | 3/2004 | Gminder et al. |
| 6,702,787 B2 | 3/2004 | Racenet et al. |
| 6,712,757 B2 | 3/2004 | Becker et al. |
| 6,726,663 B1 | 4/2004 | Dennis |
| 6,755,782 B2 | 6/2004 | Ogawa |
| 6,860,892 B1 | 3/2005 | Tanaka et al. |
| 6,918,924 B2 | 7/2005 | Lasheras et al. |
| 6,923,759 B2 | 8/2005 | Kasahara et al. |
| 6,942,671 B1 | 9/2005 | Smith |
| 6,981,966 B2 | 1/2006 | Green et al. |
| 6,989,003 B2 | 1/2006 | Wing et al. |
| 7,008,416 B2 | 3/2006 | Sakaguchi et al. |
| 7,025,747 B2 | 4/2006 | Smith |
| 7,052,454 B2 | 5/2006 | Taylor |
| 7,056,321 B2 | 6/2006 | Pagliuca et al. |
| 7,077,803 B2 | 7/2006 | Kasahara et al. |
| 7,083,626 B2 | 8/2006 | Hart et al. |
| 7,104,657 B2 | 9/2006 | Sherwin |
| 7,105,009 B2 | 9/2006 | Johnson et al. |
| 7,112,185 B2 | 9/2006 | Hart et al. |
| 7,163,525 B2 | 1/2007 | Franer |
| 7,198,598 B2 | 4/2007 | Smith et al. |
| 7,207,347 B2 | 4/2007 | Olshanetsky et al. |
| 8,100,929 B2 | 1/2012 | Franer et al. |
| 2002/0022762 A1 | 2/2002 | Beane et al. |
| 2002/0065450 A1 | 5/2002 | Ogawa |
| 2002/0068923 A1 | 6/2002 | Caldwell et al. |
| 2002/0103420 A1 | 8/2002 | Coleman et al. |
| 2002/0161387 A1 | 10/2002 | Blanco |
| 2003/0004529 A1 | 1/2003 | Tsonton et al. |
| 2003/0085373 A1 | 5/2003 | Dehdashtian |
| 2003/0130674 A1 | 7/2003 | Kasahara et al. |
| 2003/0139756 A1 | 7/2003 | Brustad |
| 2003/0195472 A1 | 10/2003 | Green et al. |
| 2004/0034339 A1 | 2/2004 | Stoller et al. |
| 2004/0106942 A1 | 6/2004 | Taylor et al. |
| 2004/0167559 A1 | 8/2004 | Taylor et al. |
| 2004/0220452 A1 | 11/2004 | Shalman |
| 2004/0230161 A1 | 11/2004 | Zeiner |
| 2004/0256004 A1 | 12/2004 | Kessell et al. |
| 2005/0033342 A1 | 2/2005 | Hart et al. |
| 2005/0043683 A1 | 2/2005 | Ravo |
| 2005/0059865 A1 | 3/2005 | Kahle et al. |
| 2005/0059934 A1 | 3/2005 | Wenchell et al. |
| 2005/0070946 A1 | 3/2005 | Franer et al. |
| 2005/0077688 A1 | 4/2005 | Voegele et al. |
| 2005/0077689 A1 | 4/2005 | Hueil |
| 2005/0096605 A1 | 5/2005 | Green et al. |
| 2005/0131349 A1 | 6/2005 | Albrecht et al. |
| 2005/0165277 A1 | 7/2005 | Carrillo et al. |
| 2005/0203543 A1 | 9/2005 | Hilal et al. |
| 2005/0216028 A1 | 9/2005 | Hart et al. |
| 2005/0241647 A1 | 11/2005 | Nguyen et al. |
| 2005/0288622 A1 | 12/2005 | Albrecht et al. |
| 2006/0020165 A1 | 1/2006 | Adams |
| 2006/0047240 A1 | 3/2006 | Kumar et al. |
| 2006/0052666 A1 | 3/2006 | Kumar et al. |
| 2006/0068360 A1 | 3/2006 | Boulais |
| 2006/0069312 A1 | 3/2006 | O'Connor |
| 2006/0100485 A1 | 5/2006 | Arai et al. |
| 2006/0122556 A1 | 6/2006 | Kumar et al. |
| 2006/0122557 A1 | 6/2006 | Kumar et al. |
| 2006/0135972 A1 | 6/2006 | Zeiner |
| 2006/0135977 A1 | 6/2006 | Thompson et al. |
| 2006/0135978 A1 | 6/2006 | Franer |
| 2006/0149137 A1 | 7/2006 | Pingleton et al. |
| 2006/0199998 A1 | 9/2006 | Akui et al. |
| 2006/0211916 A1 | 9/2006 | Kasahara et al. |
| 2006/0217665 A1* | 9/2006 | Prosek ............ 604/167.02 |
| 2006/0235455 A1 | 10/2006 | Oshida |
| 2006/0276688 A1 | 12/2006 | Surti |
| 2006/0293559 A1 | 12/2006 | Grice et al. |
| 2007/0021713 A1 | 1/2007 | Kumar et al. |
| 2007/0129719 A1 | 6/2007 | Kendale et al. |
| 2007/0142709 A1 | 6/2007 | Martone et al. |
| 2007/0149931 A1 | 6/2007 | Cannon et al. |
| 2007/0149993 A1 | 6/2007 | Kasahara et al. |
| 2007/0185453 A1 | 8/2007 | Michael et al. |
| 2007/0191759 A1 | 8/2007 | Stoller et al. |
| 2007/0204890 A1 | 9/2007 | Torii |
| 2007/0225566 A1 | 9/2007 | Kawanishi |
| 2007/0244361 A1 | 10/2007 | Ikeda et al. |
| 2009/0005799 A1 | 1/2009 | Franer et al. |

FOREIGN PATENT DOCUMENTS

| | | |
|---|---|---|
| EP | 0344907 | 12/1989 |
| EP | 0517248 | 12/1992 |
| EP | 0567142 | 10/1993 |
| EP | 568383 A1 | 11/1993 |
| EP | 570802 A1 | 11/1993 |
| EP | 664101 A1 | 7/1995 |
| EP | 0696459 A1 | 2/1996 |
| EP | 731718 A1 | 9/1996 |
| EP | 845960 A1 | 6/1998 |
| EP | 0873721 | 10/1998 |
| EP | 875256 A1 | 11/1998 |
| EP | 890342 A1 | 1/1999 |
| EP | 898971 A2 | 3/1999 |
| EP | 0972493 A2 | 1/2000 |
| EP | 1210904 A2 | 6/2002 |
| EP | 1284664 A1 | 2/2003 |
| EP | 1312318 A1 | 5/2003 |
| EP | 1323373 A2 | 7/2003 |
| EP | 1348386 A1 | 10/2003 |
| EP | 1350477 | 10/2003 |
| EP | 1459688 A1 | 9/2004 |
| EP | 1629787 A1 | 7/2006 |
| EP | 1679043 A1 | 7/2006 |
| EP | 1698291 A1 | 9/2006 |
| EP | 1707133 A1 | 10/2006 |
| EP | 1707135 A1 | 10/2006 |
| EP | 1709918 | 10/2006 |
| EP | 1834571 A1 | 9/2007 |
| EP | 1834573 A1 | 9/2007 |
| EP | 1997446 | 12/2008 |
| JP | 61036718 A | 2/1986 |
| JP | 3106329 A | 5/1991 |
| JP | 4020324 A | 1/1992 |
| JP | 4158825 A | 6/1992 |
| JP | 4170929 A | 6/1992 |
| JP | 4329510 A2 | 11/1992 |
| JP | 5192294 A | 8/1993 |
| JP | 5199979 A | 8/1993 |
| JP | 5207962 A | 8/1993 |
| JP | 6133927 A | 5/1994 |
| JP | 6169879 A | 6/1994 |
| JP | 6304121 A | 11/1994 |
| JP | 7178039 A | 7/1995 |
| JP | 7246187 A | 9/1995 |
| JP | 7-509626 A | 10/1995 |
| JP | 7289501 A | 11/1995 |
| JP | 7313442 A | 12/1995 |
| JP | 8154888 A | 6/1996 |
| JP | 8173372 A | 7/1996 |
| JP | 10043128 A | 2/1998 |
| JP | 11146882 A | 6/1999 |
| JP | 2002224014 A | 8/2002 |
| JP | 2002238906 A | 8/2002 |
| JP | 2003284686 A | 10/2003 |
| JP | 2004016455 A | 1/2004 |
| JP | 2004267583 A | 9/2004 |
| JP | 2005253543 A | 9/2005 |
| JP | 2005319101 A2 | 11/2005 |
| JP | 2007-501660 A | 2/2007 |
| WO | WO-9407552 A1 | 4/1994 |

(56) References Cited

FOREIGN PATENT DOCUMENTS

| | | |
|---|---|---|
| WO | WO-9532019 | 11/1995 |
| WO | WO-9604946 | 2/1996 |
| WO | WO-9740759 A1 | 11/1997 |
| WO | WO-0189371 A1 | 11/2001 |
| WO | WO-0230305 | 4/2002 |
| WO | WO-02078527 A2 | 10/2002 |
| WO | WO-02096307 A2 | 12/2002 |
| WO | WO-03011154 A2 | 2/2003 |
| WO | WO-2004043275 A1 | 5/2004 |
| WO | WO-2005016133 A1 | 2/2005 |
| WO | WO-2005097019 A2 | 10/2005 |
| WO | WO-2005097234 A2 | 10/2005 |
| WO | WO-2009005986 A1 | 1/2009 |

OTHER PUBLICATIONS

International Search Report for PCT/US2008/066629, dated Sep. 12, 2008.

PCT International Search Report for PCT/US2008/085472, dated Mar. 24, 2009.

* cited by examiner

DUCKBILL SEAL WITH FLUID DRAINAGE FEATURE

CROSS REFERENCE TO RELATED APPLICATIONS

This application is a continuation of U.S. patent application Ser. No. 11/771,263 filed on Jun. 29, 2007 and entitled "Duckbill Seal with Fluid Drainage Feature," which is hereby incorporated by reference in its entirety.

FIELD OF THE INVENTION

This application relates to trocar assemblies, and more particularly, to seal assemblies often used in trocar assemblies.

BACKGROUND OF THE INVENTION

Surgical procedures often require a surgeon to gain access to a cavity in a patient's body. Generally, when such a procedure is required, an incision is made in an exterior wall of the cavity and an instrument is inserted into the working channel created by the incision. One common instrument used in such a procedure is a trocar assembly. Trocar assemblies include a variety of components, but generally can include a trocar cannula, a trocar obturator, and a trocar housing. In many designs, in order to access the body cavity, the trocar cannula is directed through the skin and the trocar obturator is inserted through an interior lumen defined by the cannula. The trocar obturator is then used to penetrate the skin, which has often already had an incision made in it with a scalpel or similar device, and access the body cavity. More specifically, in some designs, applying pressure against a proximal end of the trocar obturator allows a sharp point at a distal end of the trocar obturator to be forced through the skin until it enters the body cavity. Then, the trocar cannula is inserted through the perforation made by the trocar obturator and the trocar obturator is withdrawn, leaving the inner lumen of the trocar cannula as a path to access the body cavity from outside of the body.

The trocar housing can be joined to a proximal end portion of the trocar cannula, and further, the housing can define a working chamber with an open distal end portion that is in communication with the interior lumen of the cannula. Just as the interior lumen can receive the obturator, it can also receive other elongated surgical instruments such that the instruments can be axially extended into and withdrawn from the cannula through the proximal end portion of the working chamber defined by the trocar housing. For example, in order to allow a surgeon to more easily see during a procedure, an endoscope can be inserted through the cannula and proximal or into the body cavity.

It is common for a sealing assembly or sealing device to be used in the trocar assembly. Sealing assemblies generally help prevent fluid or gas from escaping during surgical procedures. Such prevention is needed, especially during certain minimally invasive surgical procedures, in which an insufflation gas is used to expand a body cavity. However, it can be difficult to maintain the internal gas pressure because during the course of the procedure instruments are typically passed into and out of the trocar assembly. Accordingly, a sealing assembly, and often two sealing assemblies, are generally provided in the trocar assembly. The sealing assembly can seal against an outer surface of inserted instruments and thus can prevent fluids and insufflation gas from leaving and/or entering the body cavity through the trocar cannula.

In instances where two sealing assemblies are provided, the one that is a top, or proximal, seal is usually designed to seal around a surgical instrument when it is present, and the bottom, or distal, seal is usually designed for sealing the trocar cannula when the instrument is not present. One type of distal seal is a "duckbill" seal. A duckbill seal assembly generally includes a pair of opposed valve members which open and close in much the same manner a duck opens and closes its bill. Further, they can include a straight wall angle which defines a flex point for the opening and closing of the assembly, or alternatively, they can include multi-angled walls that can serve the same purpose but that can also have improved tear resistance and buckling prevention.

While such sealing assemblies are effective to prevent fluids and insufflation gas from leaving and/or entering the body cavity through the trocar cannula, fluids that can accumulate on the seal can often be wiped onto the instruments when they are being inserted therethrough. This is especially problematic for instruments such as endoscopes because fluid is often wiped directly onto the camera lens and thus obscures the surgeon's view.

Accordingly, there is a need for a seal assembly that minimizes the accumulation of fluids on surgical instruments passed into and out of a trocar assembly.

SUMMARY OF THE INVENTION

Trocars are generally provided having one or more seal assemblies for selectively promoting movement of fluid away from a central portion of the seal assemblies. In one embodiment, a seal assembly for use in a trocar assembly is provided and includes a seal body configured to selectively open the seal assembly in response to an object being inserted into the seal body. In an exemplary embodiment, an inner surface of the seal body is configured to selectively promote movement of fluid away from a central portion of the seal body toward a peripheral portion of the seal body. In one embodiment, the central portion of the seal body is located at a more proximal position than the peripheral portion of the seal body. Further, the inner surface of the seal body can be formed by any number of geometric shapes, but in two exemplary embodiments, the inner surface of the seal body extends in a substantially linear manner from the central portion to the peripheral portion, or alternatively, the inner surface of the seal body extends in a substantially arcuate manner from the central portion to the peripheral portion. In one embodiment, the seal assembly is a duckbill seal assembly.

In another embodiment of a seal assembly for use in a trocar assembly, a seal body having a longitudinal axis extending therethrough and a transverse plane substantially perpendicular to the longitudinal axis is provided, as is a plurality of opposed seal elements extending distally at an acute angle with respect to the transverse plane from a proximal end of the seal body. The opposed seal elements can include inner and outer surfaces that meet at a seal face located at a distal end of the seal body, and further, the opposed seal elements can be configured to selectively open and substantially close the seal face. In an exemplary embodiment, the inner surfaces of the seal elements can be configured to selectively promote movement of fluid away from a central portion of the seal elements toward a peripheral portion of the seal elements at the seal face. In one embodiment, the central portion of each of the inner surfaces of the seal elements is located at a more proximal position than the peripheral portion of the seal elements at the seal face. Further, the inner surfaces of each of the seal elements can be formed by any number of geometric shapes, but in two exemplary embodiments, the inner surfaces extend in a substantially linear manner from the central portion to the peripheral portion, or alternatively, the inner surfaces of each of the seal elements extend in a substantially arcuate manner from the central portion to the peripheral portion. In another embodiment, the seal body can include one or more channels formed in the distal end of the seal body and the one or more channels can be adapted to receive fluid that is moved away from the central portion of the seal elements. In one embodiment, the seal assembly is a duckbill seal assembly. In yet another embodiment, the plurality of seal elements is two seal elements.

In one embodiment of a trocar assembly, a cannula extending from a housing is provided such that the housing and the cannula define a working channel sized and configured to receive a surgical instrument. At least partially located in the working channel can be a seal assembly, and the seal assembly can include a seal body with a longitudinal axis extending therethrough and a transverse plane substantially perpendicular to the longitudinal axis. Further, a plurality of opposed seal elements can extend distally at an acute angle with respect to the transverse plane from a proximal end of the seal body. The opposed seal elements can include inner and outer surfaces that meet at a seal face at a distal end of the seal body such that the seal elements can be configured to selectively open and substantially close the seal face. In an exemplary embodiment, the inner surfaces of the seal elements can be configured to selectively promote movement of fluid away from a central portion of the seal elements toward a peripheral portion of the seal elements at the seal face. In one embodiment, the central portion of each of the inner surfaces of the seal elements is located at a more proximal position than the peripheral portion of the seal elements at the seal face. Further, the inner surfaces of each of the seal elements can be formed by any number of geometric shapes, but in two exemplary embodiments, the inner surfaces extend in a substantially linear manner from the central portion to the peripheral portion, or alternatively, the inner surfaces of each of the seal elements extend in a substantially arcuate manner from the central portion to the peripheral portion. In one embodiment, the seal assembly of the trocar assembly is a duckbill seal assembly. While the trocar assembly can include one seal assembly, in another embodiment it can include two seal assemblies such that a second seal assembly can be proximally spaced from the first seal assembly, and further, similar to the first seal assembly, the second seal assembly can also be configured to selectively open and substantially close.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices disclosed herein. One or more examples of these embodiments are illustrated in the accompanying drawings. Those skilled in the art will understand that the devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The trocar described herein includes a seal assembly that is constructed to provide for selective movement of fluid away from a central portion of a seal body toward a peripheral portion of the seal body. This selective movement is achieved by using various geometric configurations to form the seal body. Movement of fluid away from the central portion of the seal body provides a number of advantages, including reducing the amount of fluid that can accumulate on the seal so as to be wiped onto instruments, such as an endoscope, as they are passed in and out of a trocar assembly during a surgical procedure.

Apart from the seal assembly, in accordance with the present disclosure, the general structure of the trocar assembly does not generally form part of the present invention. As such, a person skilled in the art will certainly appreciate that the present seal assembly can be adapted for use with a variety of trocar assemblies without departing from the spirit of the invention disclosed herein. Further, although the seal assembly as disclosed is generally described as being a duckbill seal assembly for a trocar assembly, a person skilled in the art will appreciate that the designs discussed herein can be equally applied to any seal assembly, not just duckbill seal assemblies, and other devices that utilize seal assemblies or similar type components in order to at least partially block off one portion of a device from another, not just trocar assemblies.

Figure 1:
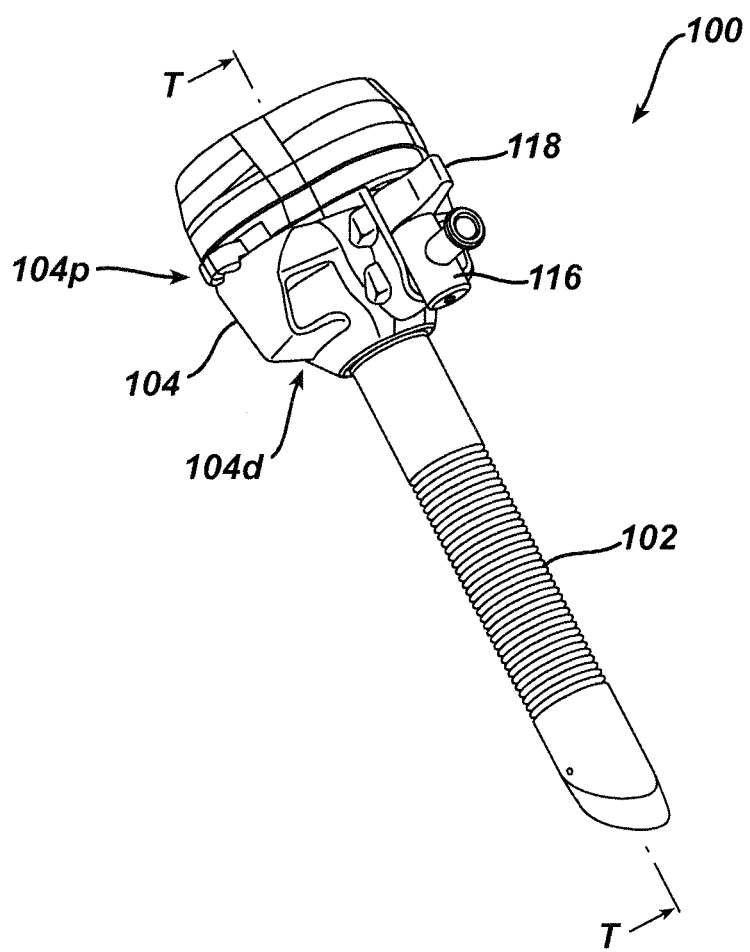
FIG. 1 is an isometric view of one exemplary embodiment of a trocar assembly.
Figure 2:
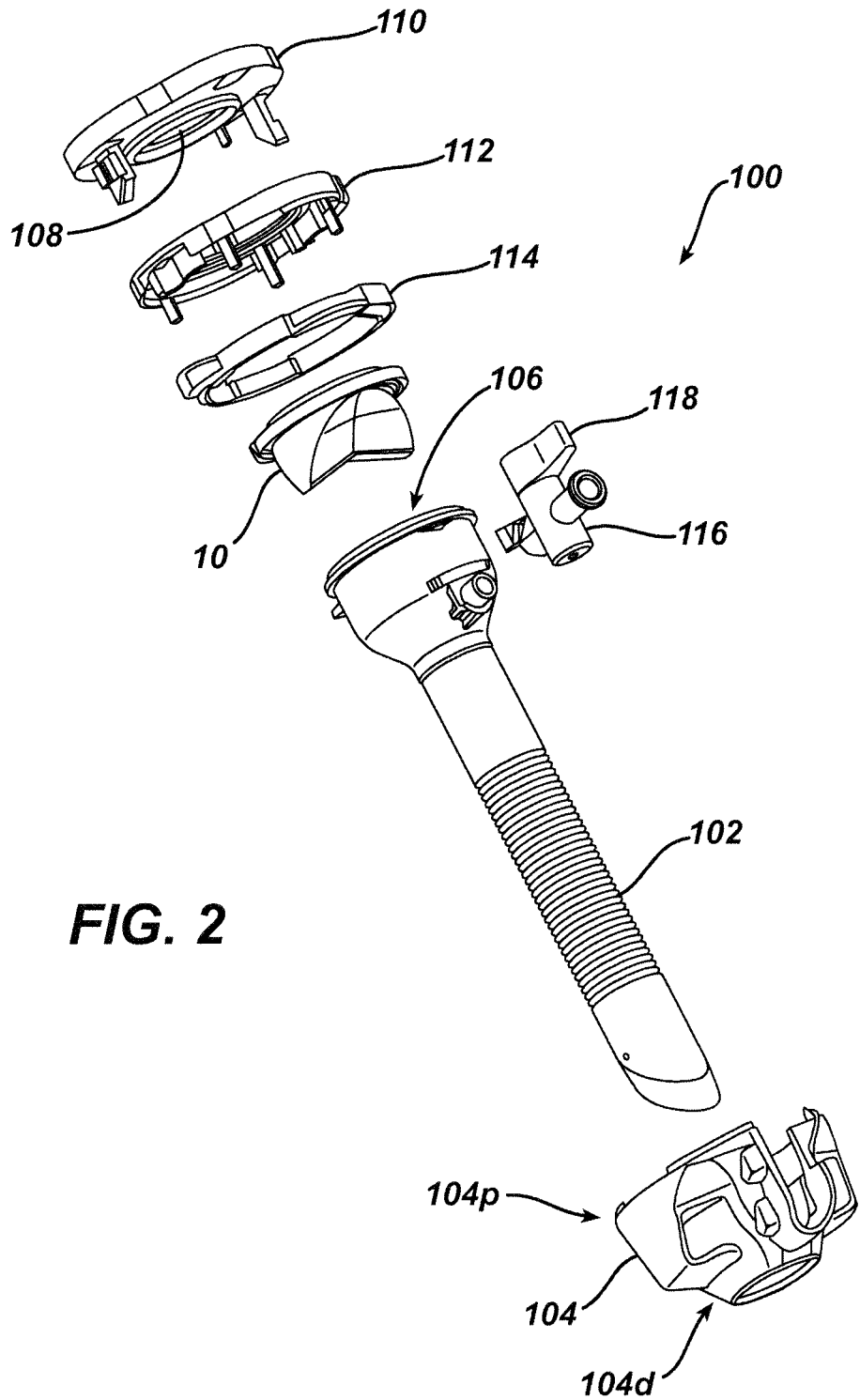
FIG. 2 is an isometric exploded view of the trocar assembly of FIG. 1 with one exemplary embodiment of a seal assembly.
Figure 3:
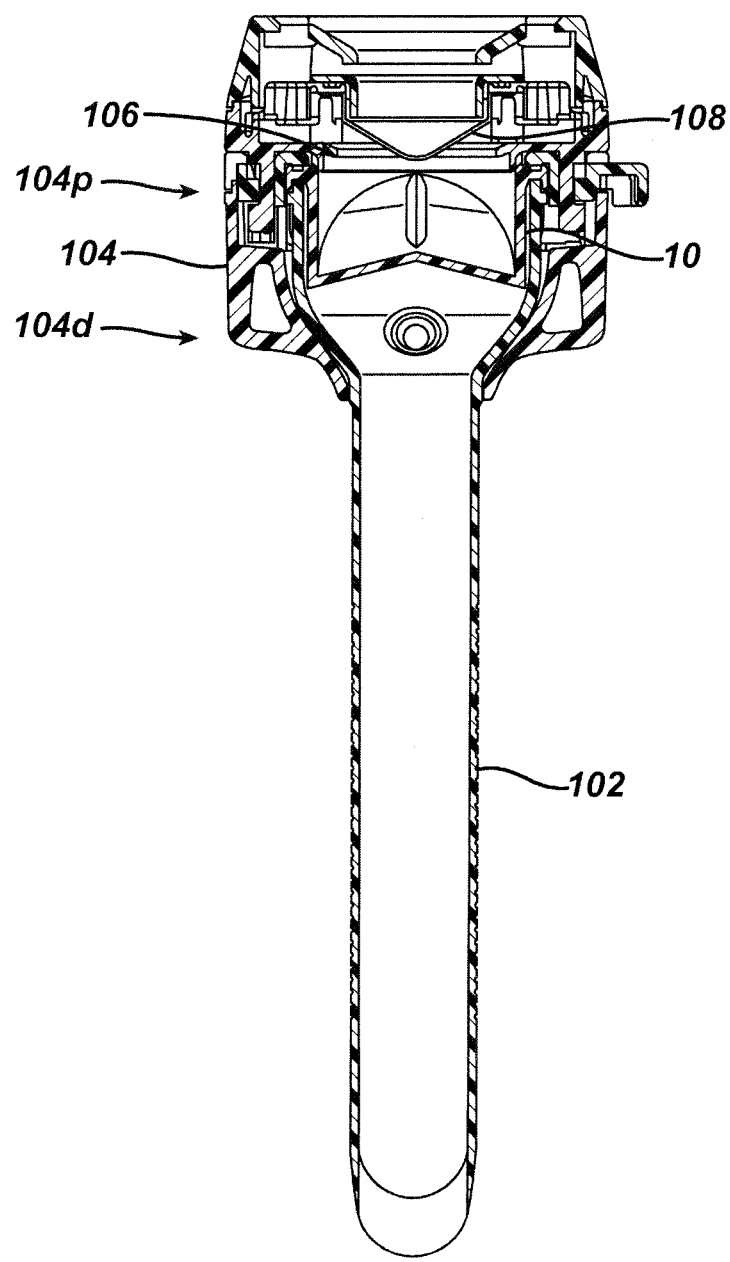
FIG. 3 is a side cross-sectional view of the trocar assembly of FIG. 1 taken at line T-T.
Figure 4:
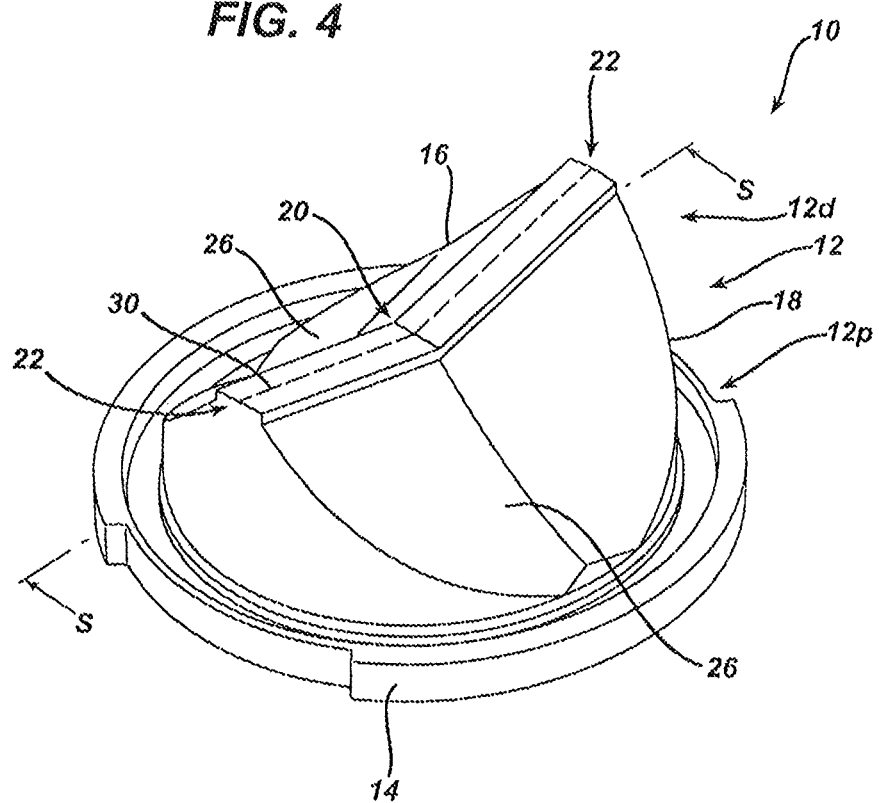
FIG. 4 is an isometric view of the exemplary embodiment of the seal assembly of FIG. 2.
Figure 5:
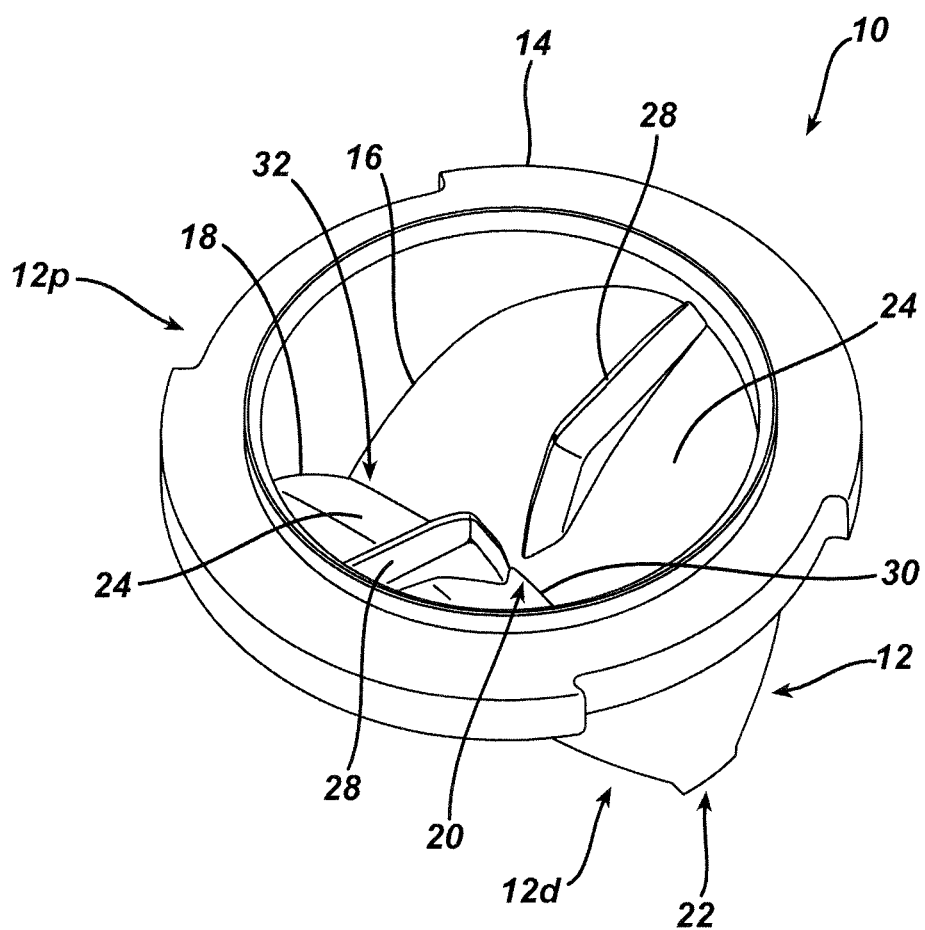
FIG. 5 is a top perspective view of the seal assembly of FIG. 4.
Figure 6:
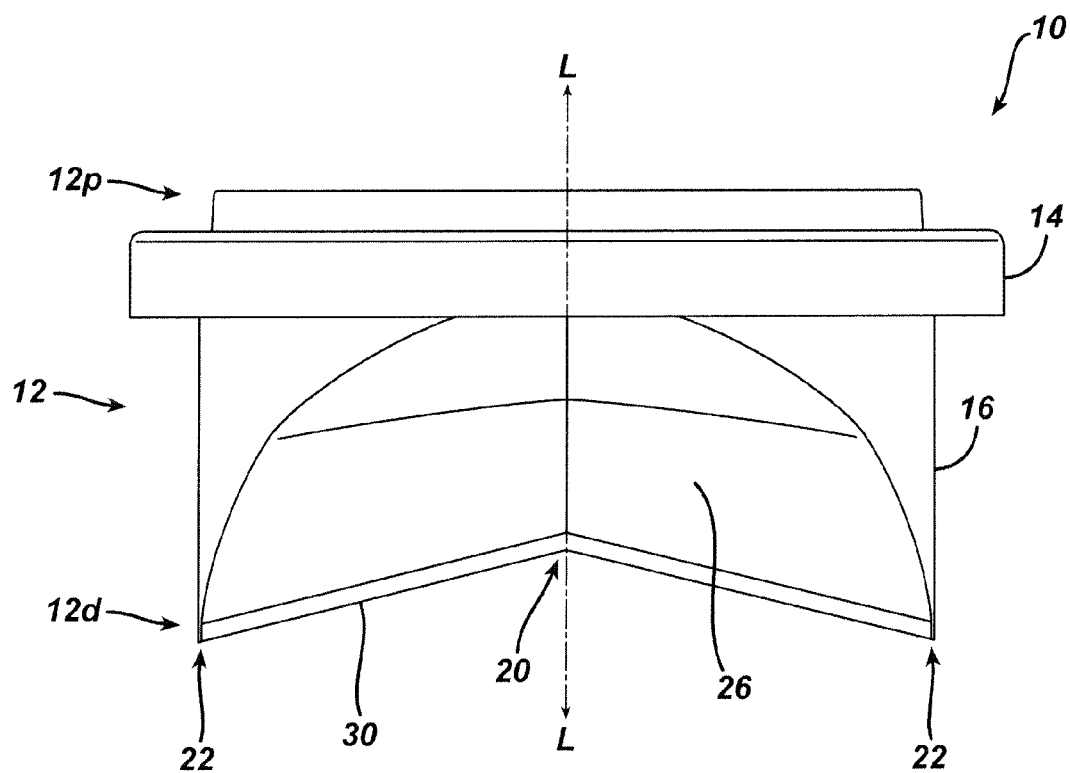
FIG. 6 is a side view of the seal assembly of FIG. 4.
Figure 7:
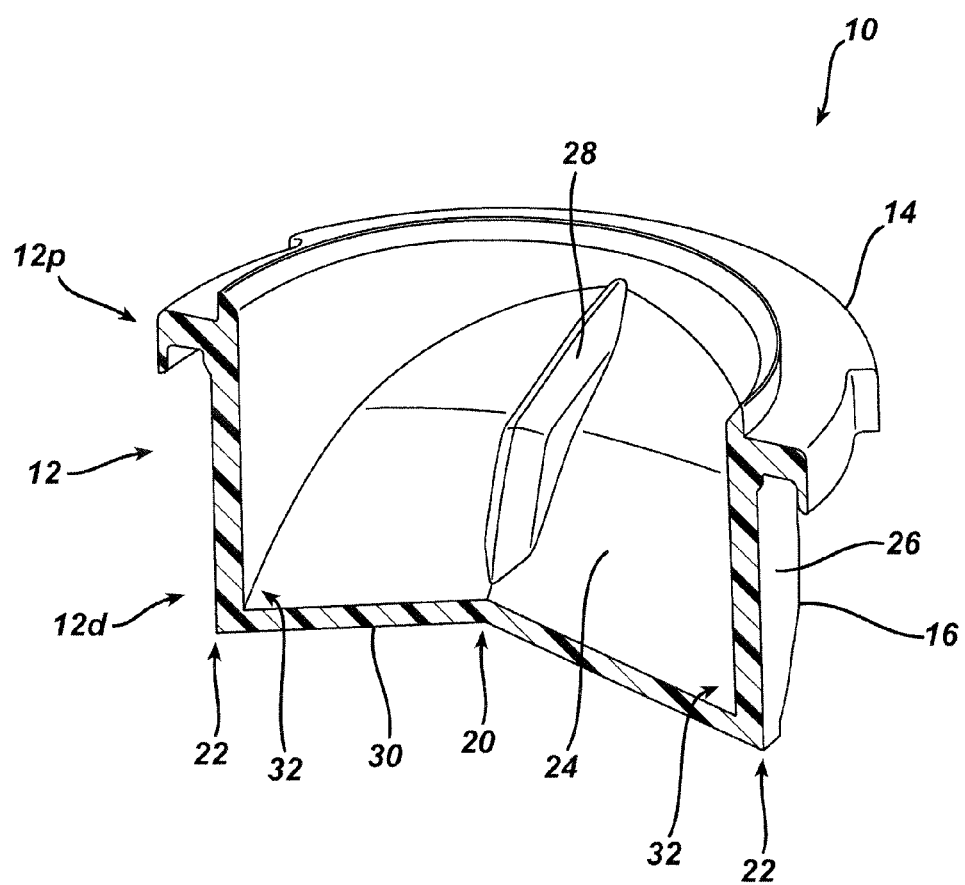
FIG. 7 is an isometric cross-sectional view of the seal assembly of FIG. 4 taken at line S-S.
Figure 8:
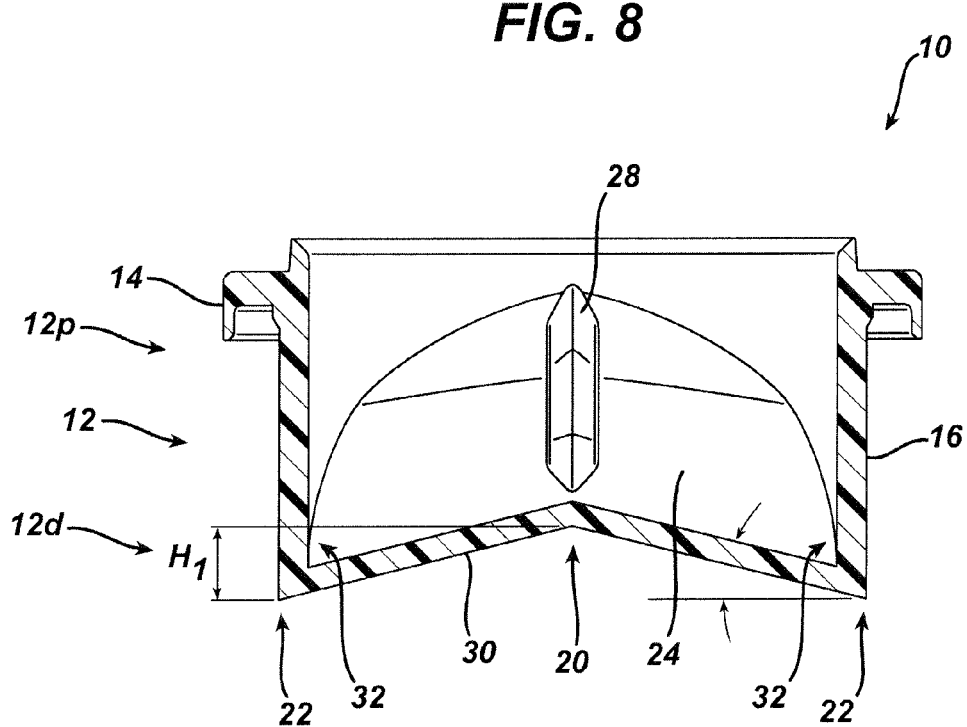
FIG. 8 is a side cross-sectional view of the seal assembly of FIG. 4 taken at line S-S.
Figure 9:
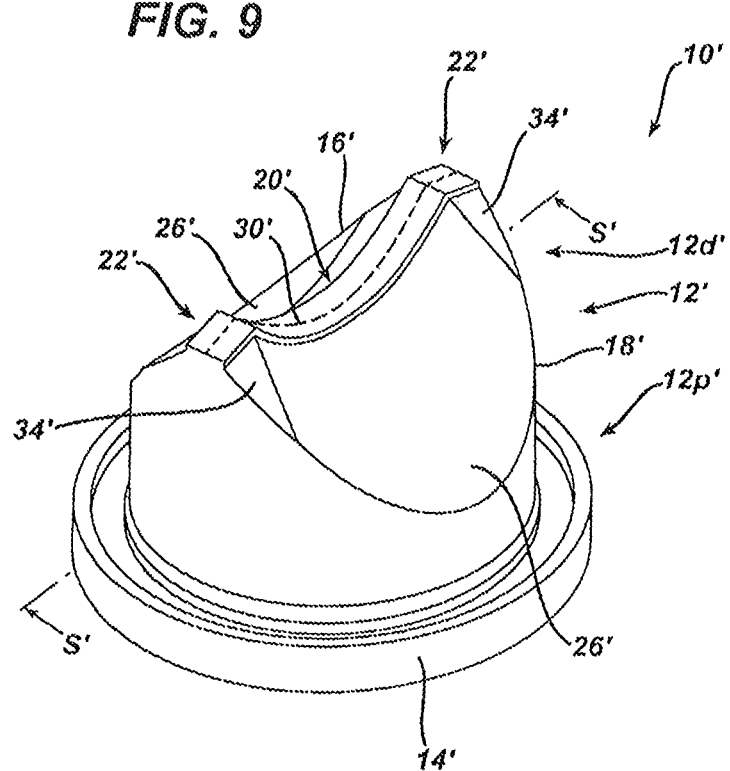
FIG. 9 is an isometric view of another exemplary embodiment of a seal assembly.
Figure 10:
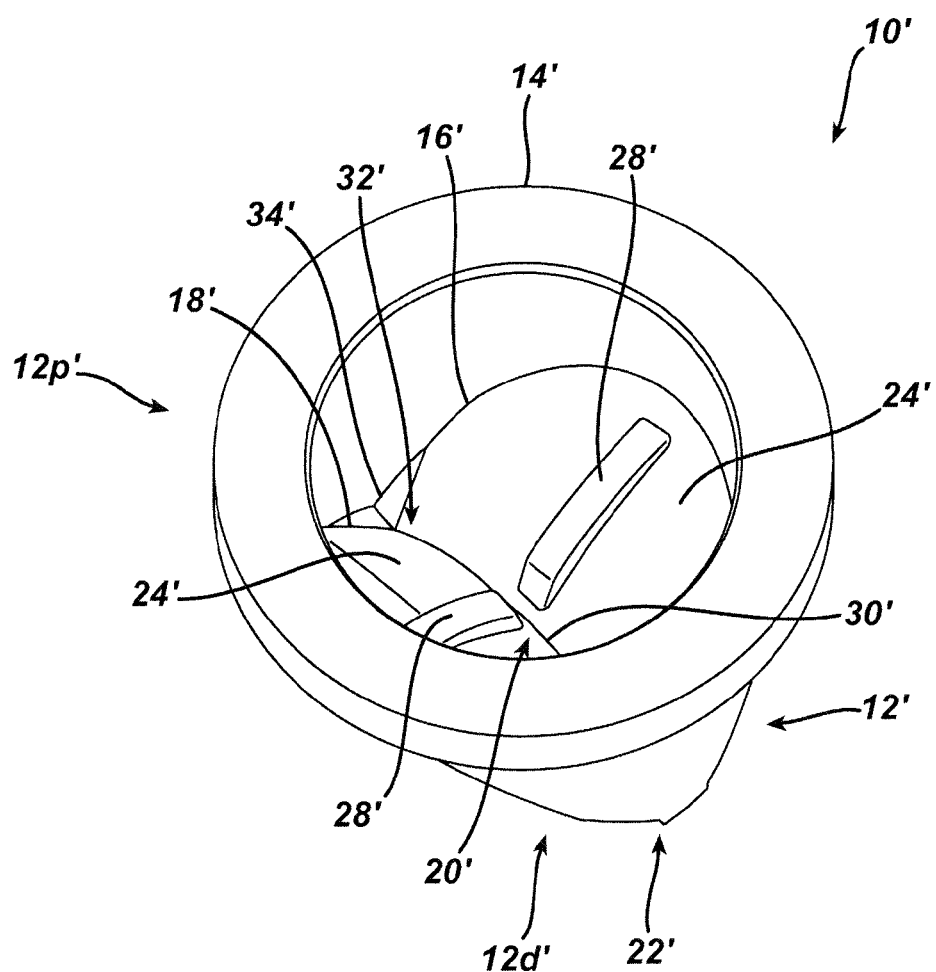
FIG. 10 is a top perspective view of the seal assembly of FIG. 9.
Figure 11:
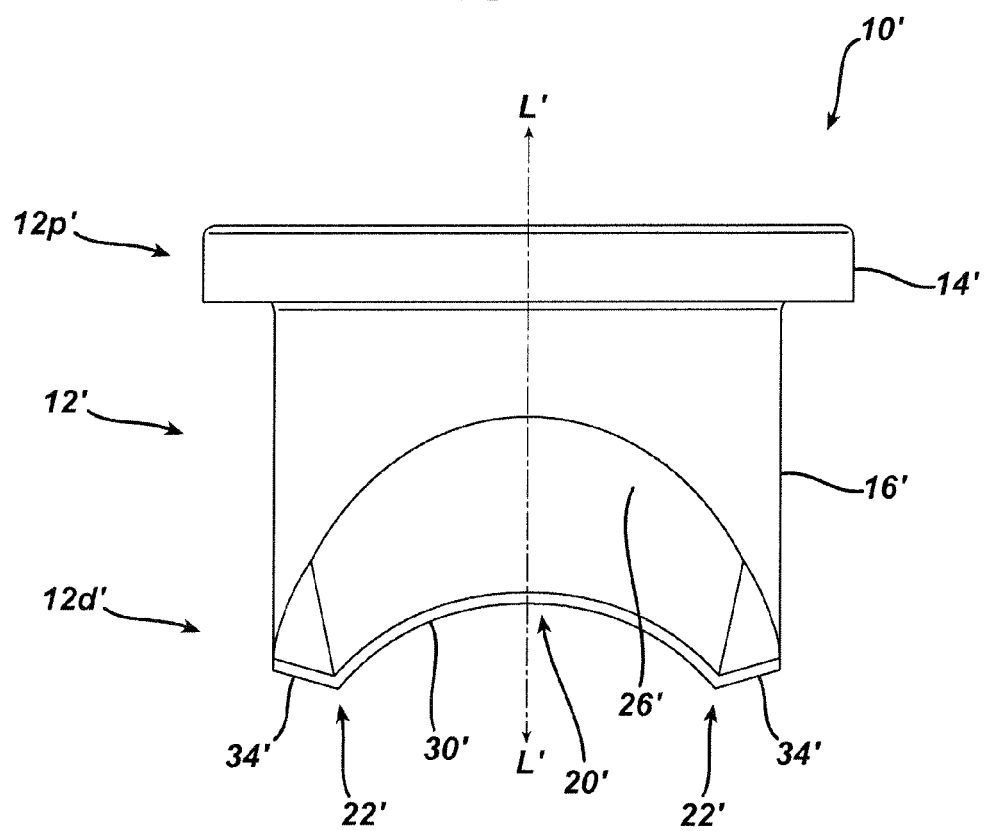
FIG. 11 is a side view of the seal assembly of FIG. 9.
Figure 12:
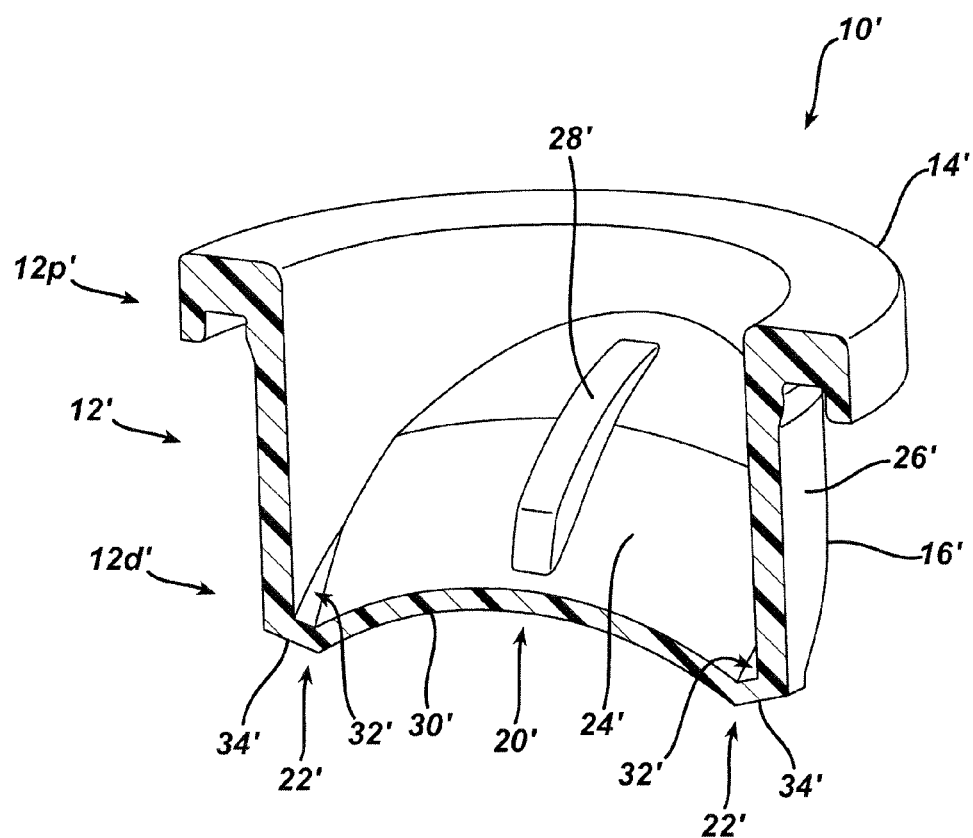
FIG. 12 is an isometric cross-sectional view of the seal assembly of FIG. 9 taken at line S'-S'.
Figure 13:
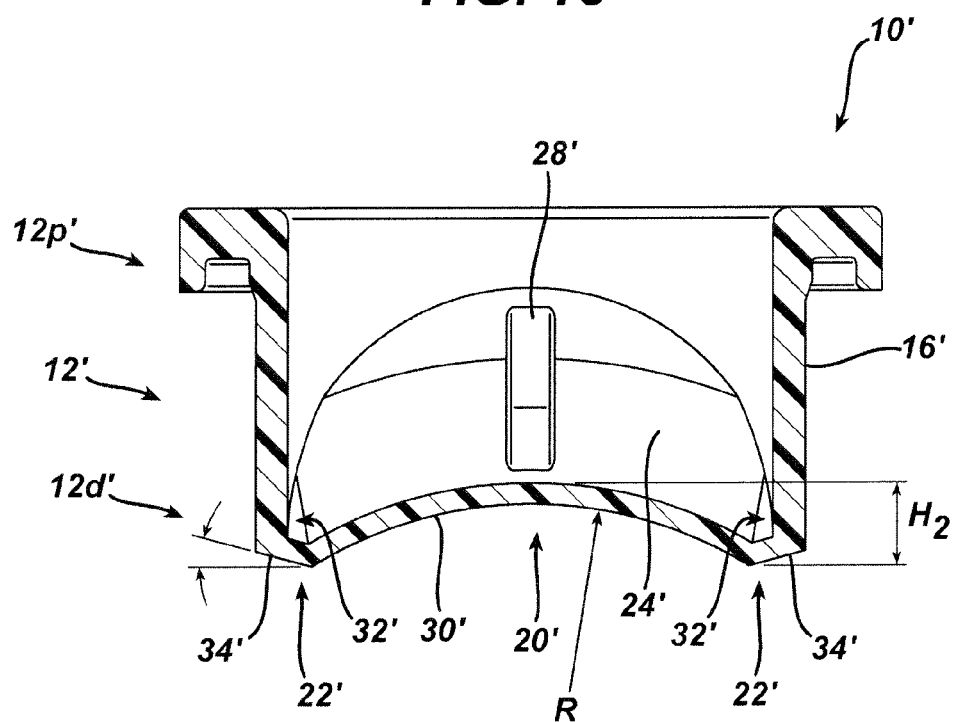
FIG. 13 is a side cross-sectional view of the seal assembly of FIG. 9 taken at line S'-S'.

Referring to FIGS. 1-3, a trocar assembly 100 can generally include a trocar cannula 102 and a trocar housing (or handle) 104. Further, the trocar cannula 102 can define an interior lumen with an open proximal end portion and an open distal end portion. The proximal end portion can extend into and be mounted in a distal end portion 104*d* of the trocar housing 104. The trocar housing 104 can have an open proximal end portion 104*p* that can define a working channel 106. In one embodiment, the working channel 106 can include a proximal seal assembly 108 at least partially positioned therein. In an exemplary embodiment, the working channel 106 can further include a duckbill seal assembly 10, 10', also at least partially positioned therein. As shown, for example, in FIG. 3, the duckbill seal assembly 10 is positioned distal to the proximal seal assembly 108 and allows for selective sealing of the working channel 106 of the trocar housing 104. A person skilled in the art will recognize that while in an exemplary embodiment two seal assemblies are provided in the working channel 106, in other embodiments one seal assembly, or more than two seal assemblies, can also be used in the trocar assembly 100. Further, the proximal seal assembly 108 and the duckbill seal assembly 10, 10' can be secured into a desired position, at least partially within the working channel 106 in a variety of ways, such as, by snap-fitting a crown ring 110 and a gasket ring 112 together, and then securing the gasket ring 112 to the trocar housing 104. A gasket retainer ring 114 can further secure the attachment between the gasket ring 112 and the trocar housing 104. In one embodiment the trocar housing 104 can further include a stop cock valve 116 and a stop cock valve lever 118, which can work together to allow and/or prevent passage of an insufflation fluid or gas, e.g. carbon dioxide, through flexible tubing into a portion of the trocar housing 104 and the trocar cannula 102.

The proximal seal assembly 108 can be adapted to cooperate with an exterior of any instrument inserted at least partially through the trocar cannula 102 such that it can sealingly engage the exterior of the instrument and thus can prevent the passage of fluids through the trocar housing 104 when the instrument is present within the trocar assembly 100. All sorts of instruments, although primarily surgical instruments, can be inserted at least partially through the trocar cannula 102. One example of such an instrument is an endoscope or a similar device that enables visualization during minimally invasive surgical procedures. One skilled in the art will recognize that many other instruments are known for insertion into at least a portion of the trocar cannula 102, and accordingly, that the proximal seal assembly 108 can likewise sealingly engage the exterior of those instruments as well.

Referring broadly to FIGS. 4-13, a duckbill seal assembly 10, 10' can generally include a seal body 12, 12' with a proximal end 12p, 12p' and a distal end 12d, 12d', a longitudinal axis L, L' (FIGS. 6 and 11) extending through the seal body 12, 12', and a transverse plane substantially perpendicular to the longitudinal axis L, L'. The seal body 12, 12' can be configured to selectively open the seal assembly 10, 10' in response to an object being inserted into the seal body 12, 12'. Further, the proximal end 12p, 12p' of the seal body 12, 12' can include a circumferential flange 14, 14' extending beyond a width of the seal body 12, 12'.

In one embodiment, the seal body 12, 12' can be a unitary structure. In another embodiment, the seal body 12, 12' can include a plurality of opposed seal elements. In the illustrated embodiments, two seal elements 16, 16', 18, 18' comprise the seal body. In other embodiments, three or more seal elements can form the seal body. The seal elements 16, 16', 18, 18' can extend distally at an acute angle with respect to the transverse plane from the proximal end 12p, 12p' of the seal body 12, 12'. The seal elements 16, 16', 18, 18' can include a central portion 20, 20' and a peripheral portion 22, 22', as well as inner surfaces 24, 24' and outer surfaces 26, 26'. In some embodiments, one or more ribs 28, 28', or other protruding structures, can be associated with the inner surfaces 24, 24' to provide a variety of advantages including added stability, as is known to those skilled in the art. In an exemplary embodiment the inner surfaces 24, 24' of the seal elements 16, 16', 18, 18', can meet at the distal end 12d, 12d' of the seal body 12, 12' to form a seal face 30, 30', and further, the seal body 12, 12' and/or the seal elements 16, 16', 18, 18' can generally be configured to selectively open and substantially close the seal face 30, 30'.

In one aspect, inner surfaces 24, 24' of seal elements 16, 16', 18, 18' are configured such that they can selectively promote movement of fluid away from the central portion 20, 20' of the seal body 12, 12' and toward the peripheral portion 22, 22' of the seal body 12, 12'. While a variety of configurations can be used to achieve this design goal, in one embodiment the central portion 20, 20' can be positioned such that it is more proximal than the peripheral portion 22, 22'. In other words, central portion 20, 20' is raised proximally relative to the peripheral portion 22, 22'.

Before discussing the two illustrated embodiments in further detail, it should be noted that although the illustrated embodiments include the seal assembly 10, 10' with the seal body 12, 12' and the seal elements 16, 16', 18, 18', a person skilled in the art will recognize that the features as discussed herein can be easily adapted for use in a unitary seal body. However, for ease of reference, the invention will be described in the context of a seal assembly that includes a seal body 12, 12' with seal elements 16, 16', 18, 18'.

FIGS. 4-8 illustrate one embodiment as a seal assembly 10 that has inner surfaces 24 of the seal elements 16, 18 configured to selectively promote movement of fluid away from the central portion 20 of the seal elements 16, 18 and toward the peripheral portion 22 of the seal elements 16, 18 at the seal face 30. In this embodiment the central portion 20 is more proximally positioned than the peripheral portion 22. Moreover, the inner surfaces 24 of each of the seal elements 16, 18 extend in a substantially linear manner from the central portion 20 to the peripheral portion 22 at the seal face 30. The height separation $H_1$ (FIG. 8) between the proximal most portion of the seal elements 16, 18 at the central portion 20 and the distal most portion at the peripheral portion 22 can vary. Generally, however, the height separation $H_1$ can be in the range of about 0.050 to 0.250 inches. In an exemplary embodiment, the height separation $H_1$ is about 0.128 inches. Because in this embodiment, the inner surfaces 24 of seal elements 16, 18 extend in a linear manner, the orientation of the inner surfaces can also be expressed as an angle. Although the angle at which the inner surfaces slope towards the peripheral portion 22 of the of the seal element can vary, the angle with respect to horizontal is generally in the range of about 10° to 25°. In an exemplary embodiment the angle is about 14°.

FIGS. 9-13 illustrate another embodiment in which the seal assembly 10' has an arced configuration such that inner surfaces 24' of the seal elements 16', 18' are configured to selectively promote movement of fluid away from the central portion 20' of the seal elements 16', 18' and toward the peripheral portion 22' of the seal elements 16', 18' at the seal face 30'. Although functionally similar to the embodiment shown in FIGS. 4-8, the embodiment of FIGS. 9-13 features a curved inner surface of the seal elements rather than one that is linearly oriented as in FIGS. 4-8. More specifically, the central portion 20' is more proximally positioned than the peripheral portion 22'. As shown, the inner surfaces 24' of each of the seal elements 16', 18' extend in a substantially arcuate manner from the central portion 20' to the peripheral portion 22' at the seal face 30'. In one embodiment, a height separation $H_2$ (FIG. 13) between the central portion 20' and the peripheral portion 22' of the seal body 12' is in the range of about 0.050 to 0.250 inches. In an exemplary embodiment, the height separation $H_2$ is about 0.155 inches. Because in the embodiment of FIGS. 9-13 the inner surfaces 24' extend in a substantially arcuate manner, a radius of the resulting arc can be measured. Although the radius can vary, the radius can be in the range of about 0.5 to 1 inch. In an exemplary embodiment, the radius is about 0.772 inches.

Referring again to FIGS. 4-13, the distal end 12d, 12d' of the seal body 12, 12' can include one or more channels 32, 32' in peripheral regions 24, 24' of seal that can receive fluid moved away from the central portion 20, 20'. One skilled in the art will recognize that other mechanisms that can retain, store, and/or remove fluid that is moved away from the central portion 20, 20' out of the seal assembly 10, 10' can also be easily adapted for use in the seal assembly 10, 10'. By way of non-limiting examples, fluid can be directly drained from the seal assembly 10, 10' as it is removed from the central portion 20, 20', or alternatively, the seal assembly 10, 10' can include a suction tube that is able to evacuate fluid out of the seal assembly 10, 10'. As illustrated in FIGS. 9-13, the seal body 12' can also optionally include one or more chamfers 34' located at the distal end 12d' of the seal body 12'. At least one advantage provided by the chamfers 34' is that they can prevent fluid from becoming trapped in corners of the channels 32'. In the embodiment illustrated in FIG. 13, the chamfers 34' are formed at about a 15 degree angle, although a variety of angles can be used with the chamfers 34' to achieve similar results. It is understood that chamfers can also be included in the seal body 12 illustrated in FIGS. 4-8, as well as in other designs of seal assemblies that fall within the scope of this disclosure.

Additional features that enhance the performance of the seal assembly 10, 10' can also be incorporated into the devices as disclosed herein. For example, in one embodiment, the seal elements 16, 16', 18, 18' can include multi-angled surfaces, as more thoroughly discussed in United States Publication No. 2005/0077688 of Voegele et al., filed on Sep. 17, 2004 and entitled "Multi-Angled Duckbill Seal Assembly," which is hereby incorporated by reference in its entirety.

The seal body 12, 12' can be made out a wide variety of materials. For example, in an exemplary embodiment, the seal body 12, 12' can be made of a polymer such as an elastomer, including, for example silicone or polyisoprene. A person skilled in the art will appreciate other materials can be used in the formation of the seal assembly 10,10', and particularly the seal body 12, 12' and/or the seal elements 16, 16', 18, 18'.

Further, although two different geometric designs are illustrated herein as exemplary embodiments, a person skilled in the art will appreciate that there are a variety of other designs that can also be incorporated into the seal assembly 10, 10' that can selectively promote movement of fluid away from the central portion 20, 20' of the seal elements 16, 16', 18, 18' toward the peripheral portion 22, 22' of the seal elements 16, 16', 18, 18' at the seal face 30, 30'. Similarly, the dimensions disclosed herein provide a range of possible dimensions for use in the exemplary embodiments, but a person skilled in the art will appreciate that other dimensions can be used in similar devices to achieve similar results. Many factors can affect design choices related to the geometries, shapes, dimensions, and materials selected for use in a similar seal assembly, such as the intended use, the ease of manufacturing, and the design of other assemblies that will be used in conjunction with the seal assembly 10, 10'. It is understood that geometries, shapes, dimensions, and materials not specifically disclosed herein do not depart from the spirit of the disclosed devices. Additionally, to the extent that linear or circular dimensions are used in the description of the disclosed device, such dimensions are not intended to limit the types of shapes that can be used in the seal assembly. A person skilled in the art will recognize that an equivalent to such linear and circular dimensions can easily be determined for any geometric shape. In a similar vein, although the designs disclosed herein illustrated a symmetrical design, in other embodiments, a non-symmetrical design can be used. Likewise, in one embodiment, a seal assembly can include at least one inner surface of a seal element that extends in a substantially linear manner from a central portion to a peripheral portion of the seal element at a seal face and at least one inner surface of a seal element that extends in a substantially arcuate manner from a central portion to a peripheral portion of the seal element at the seal face.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A seal assembly for use in a trocar assembly, comprising:
    a seal body having proximal and distal ends with a longitudinal axis extending therethrough and a transverse plane substantially perpendicular to the longitudinal axis, the seal body having a plurality of opposed seal elements, each having inner and outer surfaces and meeting at a seal face to form a straight line extending from a first peripheral portion to a second opposed peripheral portion at the distal end of the seal body such that the seal face has a central portion substantially aligned with the longitudinal axis of the seal body and the first and second peripheral portions are distally disposed from the central portion, the seal elements being configured to selectively open and substantially close the seal face; and
    a raised rib disposed on the inner surface of each of the plurality of opposed seal elements, the raised ribs being substantially aligned with the central portion of the seal face,
    wherein the inner surfaces of the seal elements are configured to promote movement of fluid away from the central portion of the seal face toward the first and second peripheral portions of the seal face.

2. The seal assembly of claim 1, wherein the inner surfaces of each of the seal elements extend in a substantially linear manner from the central portion to the first and second peripheral portions of each of the seal elements at the seal face.

3. The seal assembly of claim 1, wherein the inner surfaces of each of the seal elements extend in a substantially arcuate manner from the central portion to the first and second peripheral portions of the seal elements at the seal face.

4. The seal assembly of claim 3, wherein an arc extending across the first and second peripheral portions of each of the inner surfaces of the seal elements and through the central portion of each of the seal elements has a radius in the range of about 0.5 to 1 inches.

5. The seal assembly of claim 1, wherein the seal body further comprises one or more channels formed in the distal end thereof and in communication with the inner surfaces to receive fluid moved away from the central portion of the seal elements.

6. The seal assembly of claim 1, wherein the plurality of opposed seal elements is two seal elements.

7. The seal assembly of claim 1, wherein the plurality of opposed seal elements meet at the seal face at the distal end of the seal body to define a single opening extending substantially between two points on opposite sides of the seal body.

8. The seal assembly of claim 1, wherein the seal assembly is a duckbill seal assembly.

9. A seal assembly for use in a trocar assembly, comprising:
    a seal body having proximal and distal ends with a longitudinal axis extending therethrough and a transverse plane substantially perpendicular to the longitudinal axis, the seal body having a plurality of opposed seal elements, each having inner and outer surfaces and meeting at a seal face to form a straight line extending from a first peripheral portion to a second opposed peripheral portion at the distal end of the seal body such that the seal face has a central portion substantially aligned with the longitudinal axis of the seal body and the first and second peripheral portions are distally disposed from the central portion, the seal elements being configured to selectively open and substantially close the seal face;

a first raised rib disposed on the inner surface of a first seal element of the plurality of opposed seal elements, the first raised rib being substantially aligned with the central portion of the seal face; and a second raised rib disposed on the inner surface of a second seal element of the plurality of opposed seal elements, the second raised rib being substantially aligned with the central portion of the seal face and opposed to the first raised rib;

wherein the inner surfaces of the seal elements are configured to promote movement of fluid away from the central portion of the seal face toward the first and second peripheral portions of the seal face.

10. The seal assembly of claim 9, wherein the inner surfaces of each of the seal elements extend in a substantially linear manner from the central portion to the first and second peripheral portions of each of the seal elements at the seal face.

11. The seal assembly of claim 9, wherein the inner surfaces of each of the seal elements extend in a substantially arcuate manner from the central portion to the first and second peripheral portions of the seal elements at the seal face.

12. The seal assembly of claim 11, wherein an arc extending across the first and second peripheral portions of each of the inner surfaces of the seal elements and through the central portion of each of the seal elements has a radius in the range of about 0.5 to 1 inches.

13. The seal assembly of claim 9, wherein the seal body further comprises one or more channels formed in the distal end thereof and in communication with the inner surfaces to receive fluid moved away from the central portion of the seal elements.

14. The seal assembly of claim 9, wherein the plurality of opposed seal elements is two seal elements.

15. The seal assembly of claim 9, wherein the plurality of opposed seal elements meet at the seal face at the distal end of the seal body to define a single opening extending substantially between two points on opposite sides of the seal body.

16. The seal assembly of claim 9, wherein the seal assembly is a duckbill seal assembly.

* * * * *